United States Patent
Hotier et al.

(10) Patent No.: US 7,928,276 B2
(45) Date of Patent: Apr. 19, 2011

(54) PROCESS FOR PRODUCING HIGH PURITY META-XYLENE, COMPRISING SIMULATED MOVING BED ADSORPTION AND CRYSTALLIZATION

(75) Inventors: Gerard Hotier, Rueil Malmaison (FR); Philibert Leflaive, Mions (FR); Luc Wolff, Chapponnay (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 364 days.

(21) Appl. No.: 12/109,378

(22) Filed: Apr. 25, 2008

(65) Prior Publication Data

US 2008/0269535 A1   Oct. 30, 2008

(30) Foreign Application Priority Data

Apr. 26, 2007   (FR) .................................... 07 03113

(51) Int. Cl.
*C07C 7/12*   (2006.01)
(52) U.S. Cl. ......... 585/828; 585/820; 585/826; 585/812

(58) Field of Classification Search .................. None
See application file for complete search history.

(56) References Cited

U.S. PATENT DOCUMENTS

| | | | |
|---|---|---|---|
| 3,773,846 A | 11/1973 | Berger | |
| 4,326,092 A * | 4/1982 | Neuzil | 585/828 |
| 5,382,747 A | 1/1995 | Kulprathipanja | |
| 6,147,272 A * | 11/2000 | Mikitenko et al. | 585/812 |
| 2003/0069461 A1 * | 4/2003 | Leflaive et al. | 585/805 |

FOREIGN PATENT DOCUMENTS

WO   WO 99/64381 A1   12/1999

* cited by examiner

*Primary Examiner* — Tam M Nguyen
(74) *Attorney, Agent, or Firm* — Millen, White, Zelano & Branigan, P.C.

(57) ABSTRACT

The invention concerns a process for producing high purity meta-xylene, comprising a step for separation by simulated moving bed adsorption starting from an aromatic C8 feed delivering a fraction which is rich in meta-xylene and a fraction which is depleted in meta-xylene, and a step for crystallization of the meta-xylene rich fraction. The purity of the meta-xylene produced is at least 99.5%.

14 Claims, 1 Drawing Sheet

PROCESS FOR PRODUCING HIGH PURITY META-XYLENE, COMPRISING SIMULATED MOVING BED ADSORPTION AND CRYSTALLIZATION

FIELD OF THE INVENTION

The invention relates to a novel meta-xylene separation process with improved productivity and reduced running costs, starting from a mixture of aromatic C8 isomers for the production of very high purity meta-xylene which can be used for the synthesis of isophthalic acid which is itself used as a copolymer with terephthalic acid.

PRIOR ART

The prior art describes processes for producing meta-xylene associated with the co-production of one or more products such as para-xylene, ortho-xylene and ethylbenzene.

U.S. Pat. No. 4,326,092 describes an example of separation by adsorption carried out in a simulated moving bed delivering meta-xylene in a purity of at least 99.5%. However, that reference only refers to treated feeds which are depleted in ortho-xylene. That reference teaches that the ratio A/F (volume flow rate in selective pores over the volume flow rate of feed) is 1.5 for a treated feed with the following composition: 6.0% of paraffins, 27.0% of ethylbenzene, 17.8% of para-xylene, 45.1% of meta-xylene and 4.1% of ortho-xylene. In the remainder of the text, we shall use this concept of the flow rate in selective pores with respect to the volume flow rate of the feed as it is defined in said reference.

U.S. Pat. No. 4,306,107 describes a simulated moving bed liquid phase process in which meta-xylene is removed in the form of an extract. The para-xylene, ortho-xylene and a fraction of the ethylbenzene are removed as an intermediate raffinate. Finally, ethylbenzene is removed as the raffinate. The meta-xylene is produced in a purity of at least 99.5%. The adsorbent used for this separation is a sodium Y zeolite containing 2% to 7% by weight of water.

U.S. Pat. No. 4,313,015 describes a process for the continuous co-production of para-xylene and meta-xylene starting from a feed of hydrocarbons in a liquid phase simulated moving bed comprising three withdrawals. The extract is constituted by para-xylene which is too impure (99.44%) to be able to be sold under current regulations (the current regulation is a minimum of 99.7%), in a yield of 97.5%. The intermediate raffinate is constituted by ethylbenzene, ortho-xylene, meta-xylene and a little para-xylene, and finally the raffinate is principally constituted by a mixture of ortho-xylene and meta-xylene. High purity meta-xylene is then obtained by distilling the raffinate.

A process for the co-production of para-xylene and meta-xylene from a feed of hydrocarbons in a liquid phase simulated moving bed comprising three withdrawals is also described in French patent FR-2 782 714. The chromatographic column described contains at least twenty-five beds distributed over five zones. At least five beds have to be located in the zone included between the point for withdrawal of an intermediate raffinate containing meta-xylene, ortho-xylene, ethylbenzene, solvent and para-xylene and the point for withdrawing a raffinate containing meta-xylene, ortho-xylene and solvent.

Meta-xylene in a purity of more than 99% is thus obtained by distilling the raffinate. In addition to the large number of beds necessary for carrying out the process (for example 30), the hydrocarbon feed must have an ethylbenzene content of less than 5%; this constitutes something of a constraint.

The Applicant has filed a patent, U.S. Pat. No. 6,696,616, which describes a process for simulated moving bed co-production of para-xylene and meta-xylene in a chromatographic column comprising three withdrawals starting from a feed which is not limited as regards ethylbenzene, in which process an extract containing para-xylene is continuously withdrawn. The first raffinate is withdrawn continuously or discontinuously, and when the second raffinate comprising ortho-xylene and meta-xylene is withdrawn discontinuously, the process is also characterized in that the second raffinate is distilled to recover ortho-xylene and meta-xylene with a purity of at least 99%.

U.S. Pat. No. 5,510,562 also describes a process for separating C8 aromatics in which the mixture of ortho-xylene, meta-xylene, para-xylene and ethylbenzene is initially divided into two streams respectively containing para-xylene and ethylbenzene, and meta-xylene and ortho-xylene. The para-xylene is then separated from the ethylbenzene by distillation followed by crystallization, and the meta-xylene is separated from the ortho-xylene by distillation.

In all of the processes described in U.S. Pat. No. 4,313,015, FR-2 782 714 and U.S. Pat. No. 5,510,562 and in U.S. Pat. No. 6,696,616, high purity meta-xylene (>99%) is obtained by distillation. However, the boiling points of these two compounds are very similar (i.e. respectively 139.12° C. and 144.14° C.), which renders the production of high purity meta-xylene by distillation very difficult and necessitates a large column with at least 150 to 200 plates and a very high reflux ratio, typically more than 5 to 1.

Further, if the stream of the mixture of meta-xylene and ortho-xylene which is to be separated contains impurities in the form of para-xylene and ethylbenzene, these impurities will become concentrated in the meta-xylene, rendering achievement of a purity of more than 99.0% difficult.

U.S. Pat. No. 3,773,846 and the patents described below propose a concatenation of a para-xylene production unit and purification of meta-xylene by adsorption or crystallization, and optionally an isomerization unit.

U.S. Pat. No. 3,798,282 and U.S. Pat. No. 3,825,614 present methods for meta-xylene crystallization downstream of a para-xylene crystallization unit. The crystallization techniques employed allow coarse separation of the meta-xylene crystals, which are larger than the para-xylene crystals. After this first separation, the concentrated meta-xylene can be melted and re crystallized in a second step to produce high purity meta-xylene.

U.S. Pat. No. 3,773,846 shows the advantage of an adsorption step anterior to the crystallization step to reduce the concentration of para-xylene in the meta-xylene crystallization unit. It claims a process for the simultaneous production of high purity meta-xylene and high purity para-xylene starting from a fresh feed of C8 aromatic hydrocarbons. The first zone is a selective adsorption zone producing a stream of high purity para-xylene and a stream which is depleted in para-xylene at a concentration below the binary meta-xylene-para-xylene eutectic. A step for fractionation of that depleted stream can produce a mixture of meta-xylene and ortho-xylene overhead, the ortho-xylene being in a proportion below that of the eutectic mixture. This mixture is introduced into a crystallization unit which can produce a stream of high purity meta-xylene (>99%) and a mother liquor.

U.S. Pat. No. 6,376,736 B1 (WO-A-00/64381) also employs crystallization as a meta-xylene separation technique. The first step of separation of the para-xylene and meta-xylene starting from the feed of C8 aromatics is carried out by simulated moving bed adsorption after passing the feed into a distillation column producing a bottom stream which is rich in ortho-xylene and a distillate containing mainly ethylbenzene, para-xylene and meta-xylene. For this reason, the composition of the mixture, and especially the para-xylene content, is modified by the adsorption step, which affects crystallization and requires the design of the crystallization units to be different. The crystallization step has a number of variations which hinge on successive crystallizations below the eutectic point, with or without a "crystallization drum". Said crystallization step delivers meta-xylene (MX) with a purity of at least 99.0%.

None of the patents mentioned above proposes the production of meta-xylene by a process coupling an adsorption step and a crystallization step. Further, patents U.S. Pat. No. 5,382,747 and U.S. Pat. No. 5,900,523 describe adsorption separation processes necessitating a ratio of the flow of solid to the flow of feed which is fairly high, in particular for feeds which are rich in ortho-xylene (for example >10%).

The present invention aims to produce a process for separating meta-xylene by combining a simulated moving bed adsorption step and a crystallization step which can produce very high purity meta-xylene of at least 99.5% purity, preferably at least 99.7% and more preferably at least 99.9%.

The process of the invention accomplishes the separation of very high purity meta-xylene by coupling the two processes (simulated moving bed separation and crystallization) in an original and simplified manner to create more economical conditions for the production of very high purity meta-xylene with a purity of at least 99.5%.

In this combination:
the simulated moving bed adsorption step includes the feature of being operated under less severe conditions, the purity of the meta-xylene at the outlet from the adsorption unit being lower, typically in the range 75% to 99%. However, said unit has an enhanced productivity (quantity of meta-xylene produced per unit volume of adsorbant per unit time), and this with feeds which are rich in ortho-xylene (for example more than 10%), and with a reduced solvent to feed ratio;
the crystallization step has an improved yield because of the prior enrichment of the incoming feed.

Examples of known prior art meta-xylene crystallization methods which may be cited are the Sulzer Chemtec processes described in Chemical Engineering, May 2000 and the processes described in WO-99/64381 and U.S. Pat. No. 3,773,846.

BRIEF DESCRIPTION OF THE INVENTION

Figure 1:
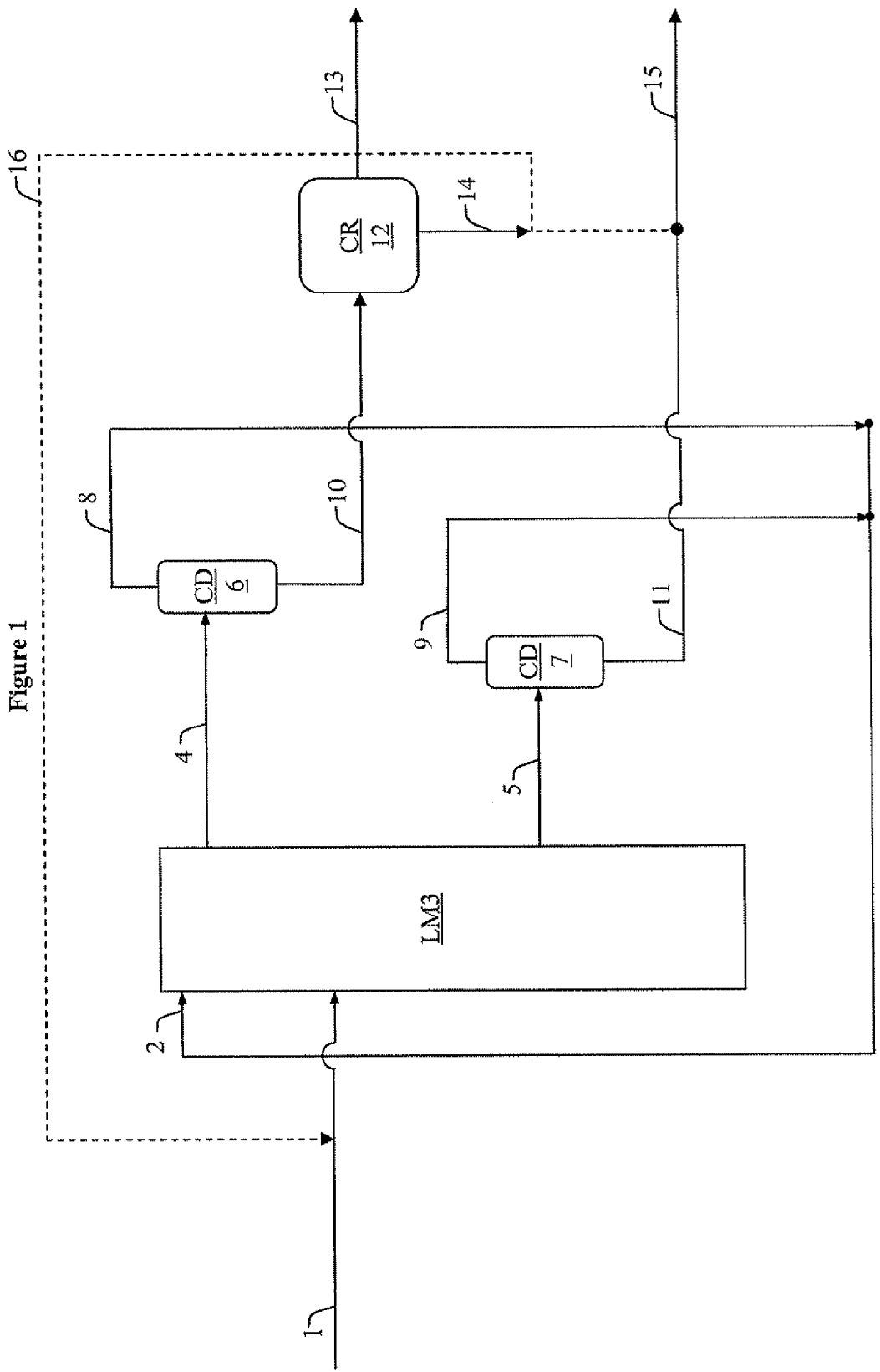
FIG. 1 corresponds to a flowchart of the process of the invention comprising a simulated moving bed column (LM3), two distillation columns (CD6) and (CD7) and a crystallization unit (CR12).

The present invention consists of a process for producing meta-xylene with a purity of more than 99.5% starting from a hydrocarbon feed essentially comprising aromatic C8 hydrocarbons, said process comprising the following steps:
1) a first step for adsorption, consisting of bringing the feed into contact, in a simulated moving bed adsorption unit (LM3), with a solid zeolitic adsorbant, said adsorption zone delivering at least two fractions, a first fraction termed the extract which is rich in meta-xylene with a purity in the range 75% to 99%, and a second fraction termed the raffinate which is depleted in meta-xylene;
2) a second step for distillation, consisting of at least one first column (CD6) which can distill the first fraction to separate out the desorbant on the one hand and meta-xylene on the other hand comprising the impurities ortho-xylene, para-xylene and ethylbenzene, in a purity of 75% to 99%, and at least one second column (CD7) which can distill the second fraction to separate out the desorbant on the one hand and a mixture on the other hand which is depleted in meta-xylene;
3) a third step for crystallization in a crystallizer (CR12), consisting of crystallizing the meta-xylene derived from step 2) at a temperature in the range −50° C. to −95° C. to obtain on the one hand crystals of meta-xylene soaked in their mother liquor, and a mother liquor part or all of which may be recycled as a mixture with fresh feed to the inlet to the simulated moving bed adsorption unit;
4) a fourth step for washing the crystals derived from step 3) at the end of which meta-xylene is recovered in a purity of at least 99.5%, preferably at least 99.7% and more preferably at least 99.9%.

DETAILED DISCLOSURE OF THE INVENTION

The invention will be better understood from an examination of FIG. 1 which shows a diagrammatic representation of the process of the invention.

Fresh feed is introduced via a line (1) into a simulated moving bed adsorption separation unit (LM3). This fresh feed contains mainly aromatic C8 compounds, xylenes and ethylbenzene, in varying proportions depending on the origin of the cut.

Optionally, this fresh feed may be supplemented with a portion (16) of the stream (14) recycled from the crystallization unit (CR12).

The simulated moving bed separation unit (LM3) comprises at least one adsorption column containing a plurality of beds of an adsorbant interconnected into a closed loop and having different selectivities for meta-xylene, ortho-xylene, para-xylene and ethylbenzene.

Said column (LM3) comprises at least four zones defined as follows:
zone 1 for meta-xylene desorption included between the desorbant injection (2) and the extract withdrawal (4);
zone 2 for ortho-xylene, para-xylene and ethylbenzene desorption included between the extract withdrawal (4) and the adsorption feed injection (1);
zone 3 for meta-xylene adsorption included between the feed injection (1) and the raffinate extraction (5);
zone 4 included between the raffinate extraction (5) and the desorbant injection (2).

Each bed is provided with a set of valves allowing the feed or desorbant to be introduced and extract or raffinate to be extracted.

The positions of the zones changes generally along the column with time by an increment corresponding to the length of a bed. The relative positions of the zones and their length are retained during successive displacements. The length of a zone is expressed as the number of beds. The period of time separating two successive displacements is termed the valve permutation time, or the period.

A complete description of a simulated moving bed process may, for example, be found in French patent FR-2 721 527.

A step for separating the extract (4) and raffinate (5) streams is carried out using the two distillation columns (CD6) and (CD7) respectively supplied withdrawals (4) and (5) and which can eliminate substantially all of the desorbant from the head of said columns, respectively via streams (8) and (9).

Meta-xylene (10) is extracted from the bottom of the column (CD6) and a distilled raffinate (11) is withdrawn from the bottom of the column (CD7), which raffinate contains ortho-xylene, para-xylene, ethylbenzene and a little meta-xylene. The desorbant recovered via lines (8) and (9) is sent to the adsorption column (LM3) using the line (2).

The stream of meta-xylene (10) is sent to at least one crystallization zone (CR12) to deliver crystals of meta-xylene and a mother liquor (14). The crystals are separated from the mother liquor, optionally taken up into suspension, washed and recovered to produce a stream of meta-xylene (13) with a purity of at least 99.5%, and preferably at least 99.7%, and still more preferably at least 99.9%.

The meta-xylene crystals are generally washed using a stream of high purity liquid meta-xylene, i.e. with a purity of more than 99.5%, preferably more than 99.7% and still more preferably more than 99.9%. Preferably, this wash is carried out at a temperature which is equal to or slightly higher than the melting point of the meta-xylene crystals to benefit from partial melting of said crystals, which contributes to supplying the stream of liquid meta-xylene necessary for washing.

The mother liquor (14) may be recycled at least in part via the stream (16) to the adsorption column (LM3) and/or be mixed with the distilled raffinate (11) to form a stream (15) which is generally sent to an isomerization unit.

Preferably, the mother liquor (14) is either 100% recycled to the adsorption column (LM3) or 100% of it is mixed with the distilled raffinate (11) to form the stream (15).

The fresh feed may optionally contain variable amounts of impurities which depend on the origin of the feed, which are essentially paraffinic and napthenic compounds.

The amount of napthenic or paraffinic impurities is advantageously below 1% by weight. Preferably, this amount is less than 0.3% by weight, and more preferably, this amount is less than 0.1% by weight.

The feed may be derived either from an aromatizing unit (i.e. for forming aromatic compounds) or from a toluene disproportionation unit or from a unit for transalkylation of toluene and C9 aromatics, or from a raffinate from a simulated moving bed para-xylene separation unit, or from raffinate 2 from a simulated moving bed para-xylene separation unit comprising two raffinate extractions (termed raffinate 1 and raffinate 2).

According to one characteristic of the process, the simulated moving bed separation unit (LM3) operates in simulated counter-current mode and includes at most 24 beds, preferably at most 15 beds.

24 beds are used when debottlenecking of an existing simulated moving bed separation unit (usually including 24 beds) is desired by coupling said unit with a crystallization unit as described in the present invention in order to increase the total meta-xylene production capacity.

According to one characteristic of the process, the adsorbant in the adsorption separation unit (LM3) may comprise at least one zeolite selected from the group consisting of an X zeolite exchanged with calcium, an X zeolite exchanged with caesium, a Y zeolite exchanged with sodium or a Y zeolite exchanged with sodium and lithium.

Preferably, a Y zeolite containing substantially only sodium is recommended. Examples of meta-selective zeolites (i.e. selective towards meta-xylene) containing sodium are described in the following patents: U.S. Pat. Nos. 4,326,092, 5,382,747, 5,900,523 and EP-A-0 712 821.

The preferred desorbant for the first separation step carried out in the adsorption column (LM3) is toluene. However, other desorbants such as indane, 1,2,4-trimethylbenzene, paramethylethylbenzene or cumene, which may be used pure or as a mixture, may also be suitable.

According to a further characteristic of the invention, the first simulated moving bed separation step may be carried out at a temperature which is generally in the range 20° C. to 250° C., preferably in the range 90° C. to 210° C., and more preferably in the range 150° C. to 170° C. and at a pressure in the range from the bubble pressure of the xylenes at the selected operating temperature and 20 bars (1 bar=$10^5$ bars).

According to a further characteristic of the invention, the volume ratio of the desorbant to the feed in the first simulated moving bed separation step carried out in the column (LM3) may be in the range 1.0 to 4.0; preferably, it is in the range 1.5 to 3.0.

According to a further characteristic of the invention, the volume ratio of the flow rate of the selective pores of the adsorbant over the flow rate of the feed in the first simulated moving bed separation step carried out in the column (LM3) may be in the range 1.0 to 4.0, preferably in the range 1.0 to 2.0.

According to a preferred characteristic of the invention, the molar composition of the feed sent to the crystallization step is within the range defined by the following 8 points:
  pure meta-xylene;
  para-xylene/meta-xylene (para-xylene 12.2%, meta-xylene 87.8%) binary eutectic;
  meta-xylene/ortho-xylene (meta-xylene 67.5%, ortho-xylene 32.5%) binary eutectic;
  meta-xylene/ethylbenzene (meta-xylene 15.8%, ethylbenzene 84.2%) binary eutectic;
  para-xylene/meta-xylene/ortho-xylene (para-xylene 7.5%, meta-xylene 62.7%, ortho-xylene 29.8%) ternary eutectic;
  para-xylene/meta-xylene/ethylbenzene (para-xylene 1.0%, meta-xylene 15.6%, ethylbenzene 83.4%) ternary eutectic;
  meta-xylene/ortho-xylene/ethylbenzene (meta-xylene 14.8%, ortho-xylene 5.4%, ethylbenzene 79.8%) ternary eutectic;
  para-xylene/meta-xylene/ortho-xylene/ethylbenzene (para-xylene 1.0%, meta-xylene 14.6%, ortho-xylene 5.3%, ethylbenzene 79.1%) quaternary eutectic.

In accordance with a preferred characteristic of the invention, the crystallization zone may be composed of one or more crystallizers, for example static crystallizers operating alternately in the cooling phase and in the heating phase.

A refrigeration unit is used to operate at a temperature in the range −50° C. to −95° C.

After obtaining the solid meta-xylene fraction, the remaining mother liquor is withdrawn from the crystallizer. The purest crystalline layer remains adhering to the plates of the static crystallizer. These crystals are then purified by heating to a temperature slightly above the crystallization point. This partial fusion washes the crystals and produces meta-xylene with a purity of at least 99.5%, preferably at least 99.7% and more preferably at least 99.9%.

The separated mother liquor (14) may be mixed with the distilled raffinate (11) to form the stream 15 and/or be recycled to the adsorption column (LM3).

Preferably, the mother liquor (14) is recycled as a function of the configuration of the complex ensemble, either 100% in the adsorption column (LM3) or 100% mixed with the distilled raffinate (11) to form the stream (15).

EXAMPLES

The invention will be illustrated by the following comparative example which is not limiting in any way.

Example 1

Prior Art

The prior art process includes a simulated moving bed separation unit which can produce meta-xylene with a purity of 99.1%.

The present example illustrates the production of meta-xylene with a purity of 99.1%. The meta-xylene was separated by simulated moving bed counter-current adsorption. The initial feed, rich in ortho-xylene, had the following composition by weight:
PX: para-xylene 3.57%;
MX: meta-xylene 55.84%;
OX: oxide 28.36%;
EB: ethylbenzene 11.79%;
TOL: toluene 0.44%.

The pilot unit used was constituted by 24 columns 1.1 m in length and 0.021 m in diameter. Each column was loaded with 240.6 g of Y zeolite exchanged with sodium with a moisture content of less than 0.1%, expressed as the loss on ignition at 900° C.

The operating temperature was 160° C.; the pressure at the recycle pump intake was maintained at 10 bars.

All of the streams were injected or withdrawn continuously with a controlled flow rate, with the exception of the raffinate which was continuously withdrawn under pressure control; the injection and withdrawal flow rates were expressed using the conditions of the process.

The total number of beds was 24.

4 beds were located between the desorbant injection and the extract withdrawal; 10 beds between the extract withdrawal and the feed injection; 7 beds between the feed injection and the raffinate withdrawal; 3 beds between the raffinate withdrawal and the desorbant injection.

The operating conditions were as follows:
Solvent: 67.71 cm$^3$/min of desorbant (100% toluene);
Extract: 48.79 cm$^3$/min;
Feed: 18.72 cm$^3$/min
Raffinate: 37.64 cm$^3$/min;
Recycle flow rate (in zone 1): 237.3 cm$^3$/min;
Valve permutation time (or period): 90.0 seconds;
Ratio of flow rate of desorbant to flow rate of feed: 3.62;
Volume ratio of flow rate in selective pores of adsorbant to flow rate of feed was 2.20.

After toluene distillation, the continuously obtained extract obtained delivered a stream of 9.47 cm$^3$/min with a meta-xylene purity of 99.4%.

The meta-xylene yield was 90.1%, giving a productivity of 0.053 T MX/m$^3$/h.

Example 2

In Accordance with the Invention

This example illustrates the case of a unit in accordance with the invention comprising an adsorption unit with 15 beds of adsorbant coupled with a crystallization zone which can produce meta-xylene with a purity of 99.7%.

The pilot unit used was constituted by 15 columns 1.1 m in length and 0.021 m in diameter. Each column was loaded with 240.6 g of Y zeolite exchanged with sodium with a moisture content of less than 0.1%, expressed as the loss on ignition at 900° C. The operating temperature was 160° C.; the pressure at the recycle pump intake was maintained at 10 bars.

All of the streams were injected or withdrawn continuously under flow rate control, with the exception of the raffinate which was continuously withdrawn under pressure control, the injection and extraction flow rates were expressed using the conditions of the process.

The total number of beds was 15, distributed as follows:
3 beds between the desorbant injection and the extract withdrawal;
6 beds between the extract withdrawal and the feed injection;
4 beds between the feed injection and the raffinate withdrawal;
2 beds between the raffinate withdrawal and the desorbant injection.

The operating conditions were as follows:
Solvent: 62.71 cm$^3$/min of desorbant (100% toluene);
Extract: 49.79 cm$^3$/min;
Feed: 21.72 cm$^3$/min
Raffinate: 34.64 cm$^3$/min;
Recycle flow rate (in zone 1): 237.3 cm$^3$/min;
Valve permutation time (or period): 90.0 seconds;
Ratio of flow rate of desorbant to flow rate of feed: 2.89;
Volume ratio of flow rate of selective pores of adsorbant to flow rate of feed was 1.90.

After toluene distillation, the continuously obtained extract obtained delivered a stream of 10.98 cm$^3$/min with a meta-xylene purity of 98.4%.

The meta-xylene yield was 89.1%, giving a productivity of 0.098 Tonnes of MX/m$^3$/h.

The crystallization zone comprised two static crystallizers operating in a manner which alternated between the cooling phase and the heating phase when the crystals were produced. A refrigeration unit was used to produce meta-xylene crystals at −60° C.

After crystallization, the mother liquor was withdrawn. The meta-xylene crystals were washed with very high purity molten meta-xylene and were simultaneously purified by partial fusion at −45° C.

The meta-xylene yield from crystallization was 96.7%.

The quantity of meta-xylene produced by the process was 10.48 cm$^3$/min; its purity was 99.7%.

The quantity of meta-xylene produced was thus greater than 11% compared with the prior art with a 0.6 point improvement in purity.

The simulated moving bed adsorption separation unit was operated with a reduced number of beds, a volume ratio of the flow rate of desorbant to the flow rate of feed which was reduced by 20% and a volume flow rate of the selective pores of the adsorbant to the feed flow rate reduced by 14%.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 07/03113, filed Apr. 26, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing very high purity meta-xylene starting from a hydrocarbon feed containing meta-xylene, ortho-xylene, para-xylene, ethylbenzene and optionally naphthenes and C8 paraffins, said process comprising a concatenation of four steps:
   1) in a first step of adsorption, consisting of bringing the feed (1) into contact, in a simulated moving bed adsorption unit (LM3) with a solid zeolitic adsorbant, said adsorption unit delivering at least two fractions, a first fraction termed the extract (4), which is rich in meta-xylene with a purity in the range 75% to 99%, and a second fraction termed the raffinate (5) which is depleted in meta-xylene;
   2) a second step comprising distillation of the first fraction (4) in at least one first column (CD6) to separate out the desorbant (8) a mixture of meta-xylene (10) in a purity of 75% to 99%, together with impurities ortho-xylene, para-xylene and ethylbenzene, and in at least one second column (CD7) distilling the second fraction to separate out the desorbant (9) from a mixture (11) which is depleted in meta-xylene;
   3) a third step, comprising crystallization, in at least one unit (CR12) crystallizing the meta-xylene derived from step 2) at a temperature in the range of −50° C. to −95° C. to obtain on the one hand crystals of meta-xylene soaked in their mother liquor, and on the other hand a mother liquor (14) part of which is recycled as a mixture with the feed (1) to the inlet to the simulated moving bed adsorption unit (LM3); and
   4) a fourth step comprising washing the crystals derived from step 3), at the end of which meta-xylene (13) is recovered in a purity of at least 99.5%.

2. A process for producing high purity meta-xylene according to claim 1, in which the simulated moving bed unit functions in counter-current mode.

3. A process for producing high purity meta-xylene according to claim 1, in which the mother liquor (14) from the crystallization unit (CR12) is integrally recycled as a mixture with fresh feed (1) to the inlet of the simulated moving bed adsorption unit (LM3).

4. A process for producing high purity meta-xylene according to claim 1, in which the mother liquor (14) derived from the crystallization unit (CR12) is integrally mixed with the distilled raffinate (11) derived from the distillation column (CD7).

5. A process for producing high purity meta-xylene according to claim 1, in which the feed has an ortho-xylene content of more than 10% by weight.

6. A process for producing high purity meta-xylene according to claim 1, in which the simulated moving bed adsorption step is carried out at a temperature of 140° C. to 180° C. on a sodium exchanged Y zeolite with a water content of less than 1% by weight.

7. A process for producing high purity meta-xylene according to claim 1, in which the desorbant used in the simulated moving bed adsorption unit is toluene.

8. A process for producing high purity meta-xylene according to claim 1, in which the volumetric ratio of the volume flow rate of desorbant to the volume flow rate of feed is in the range of 1.0 to 3.0.

9. A process for producing high purity meta-xylene according to claim 1, in which the volumetric ratio of the flow rate in selective pores of the adsorbant to the flow rate of the feed is in the range of 1.0 to 4.0 to 1.

10. A process for producing high purity meta-xylene according to claim 1, in which the adsorption unit comprises at most 24 beds.

11. A process for producing high purity meta-xylene according to claim 1, in which the molar composition of the feed sent to the crystallization step (4) is within the range defined by the following 8 points:
   pure meta-xylene;
   para-xylene/meta-xylene (para-xylene 12.2%, meta-xylene 87.8%) binary eutectic;
   meta-xylene/ortho-xylene (meta-xylene 67.5%, ortho-xylene 32.5%) binary eutectic;
   meta-xylene/ethylbenzene (meta-xylene 15.8%, ethylbenzene 84.2%) binary eutectic;
   para-xylene/meta-xylene/ortho-xylene (para-xylene 7.5%, meta-xylene 62.7%, ortho-xylene 29.8%) ternary eutectic;
   para-xylene/meta-xylene/ethylbenzene (para-xylene 1.0%, meta-xylene 15.6%, ethylbenzene 83.4%) ternary eutectic;
   meta-xylene/ortho-xylene/ethylbenzene (meta-xylene 14.8%, ortho-xylene 5.4%, ethylbenzene 79.8%) ternary eutectic;
   para-xylene/meta-xylene/ortho-xylene/ethylbenzene (para-xylene 1.0%, meta-xylene 14.6%, ortho-xylene 5.3%, ethylbenzene 79.1%) quaternary eutectic.

12. A process according to claim 8, wherein said volumetric ratio is in the range of 1.5 to 2.5.

13. A process according to claim 9, wherein said volumetric ratio is in the range of 1.0 to 2.0.

14. A process according to claim 10, wherein the adsorption unit comprises at most 15 beds.

* * * * *